US009884147B2

(12) United States Patent
Azeez

(10) Patent No.: US 9,884,147 B2
(45) Date of Patent: Feb. 6, 2018

(54) DEVICE AND METHOD FOR CLEANING NASAL CAVITIES

(71) Applicant: Kemi Azeez, Lima, OH (US)

(72) Inventor: Kemi Azeez, Lima, OH (US)

(*) Notice: Subject to any disclaimer, the term of this patent is extended or adjusted under 35 U.S.C. 154(b) by 562 days.

(21) Appl. No.: 13/739,933

(22) Filed: Jan. 11, 2013

(65) Prior Publication Data
US 2014/0200507 A1 Jul. 17, 2014

Related U.S. Application Data

(60) Provisional application No. 61/586,501, filed on Jan. 13, 2012.

(51) Int. Cl.
*A61M 3/02* (2006.01)
*A61B 17/24* (2006.01)
*A61H 35/04* (2006.01)
*A61H 33/00* (2006.01)
A61M 1/00 (2006.01)
A61M 31/00 (2006.01)
A61M 15/08 (2006.01)
(Continued)

(52) U.S. Cl.
CPC .......... *A61M 3/0258* (2013.01); *A61B 17/24* (2013.01); *A61H 33/6021* (2013.01); *A61H 35/04* (2013.01); *A61M 1/0003* (2013.01); *A61M 1/0005* (2013.01); *A61M 1/0066* (2013.01); *A61M 1/0082* (2014.02); *A61M 1/0084* (2013.01); *A61M 3/0283* (2013.01); A61B 2017/246 (2013.01); A61H 7/002 (2013.01); A61M 1/0058 (2013.01); A61M 11/006 (2014.02); A61M 15/08 (2013.01); A61M 31/00 (2013.01); A61M 2205/103 (2013.01); A61M 2205/3382 (2013.01); A61M 2205/3386 (2013.01); A61M 2205/8206 (2013.01); A61M 2210/0618 (2013.01)

(58) Field of Classification Search
CPC .... A61M 1/0058; A61M 3/02; A61M 3/0233; A61M 3/0254; A61M 3/0258; A61M 3/0275; A61M 2210/0618; A61B 17/24; A61B 2017/246; A61B 17/1688
See application file for complete search history.

(56) References Cited

U.S. PATENT DOCUMENTS

| 4,883,465 A | * | 11/1989 | Brennan | ............... A61M 27/00 604/43 |
| 5,618,550 A | * | 4/1997 | Ratcliff | .................... A61K 8/20 424/422 |
| 5,649,530 A | | 7/1997 | Ballini | |

(Continued)

OTHER PUBLICATIONS

Wet Vacuum vs. Dry Vacuum. (n.d.). Retrieved Jul. 7, 2015. <http://www.eng-tips.com/viewthread.cfm?qid=85460>.*
(Continued)

*Primary Examiner* — Bhisma Mehta
*Assistant Examiner* — Nilay Shah
(74) *Attorney, Agent, or Firm* — Porter Wright Morris & Arthur LLP

(57) ABSTRACT

A device for cleaning nasal membranes comprising a head that is inserted into a nostril. Fluid is pumped from a reservoir stored in a body of the device onto the membrane. The head rotates to remove debris from the membrane. A vacuum pump suctions the sprayed fluid and the debris into inlets and stores the used fluid in a chamber in the body.

20 Claims, 4 Drawing Sheets

(51) Int. Cl.
*A61M 11/00* (2006.01)
*A61H 7/00* (2006.01)

(56) References Cited

U.S. PATENT DOCUMENTS

| | | | |
|---|---|---|---|
| 5,906,198 A | 5/1999 | Flickinger | |
| 6,187,332 B1* | 2/2001 | Gern | A61K 9/0043 |
| | | | 424/400 |
| 6,332,891 B1* | 12/2001 | Himes | A61B 90/36 |
| | | | 606/130 |
| 6,517,511 B2 | 2/2003 | Yao | |
| 6,907,879 B2 | 6/2005 | Drinan | |
| 7,862,536 B2 | 1/2011 | Chen et al. | |
| 7,959,597 B2 | 6/2011 | Baker et al. | |
| 2003/0158527 A1* | 8/2003 | Mezzoli | A61H 35/04 |
| | | | 604/275 |
| 2005/0175960 A1* | 8/2005 | Wiek | A61C 17/222 |
| | | | 433/88 |
| 2008/0154183 A1* | 6/2008 | Baker et al. | 604/28 |
| 2008/0221507 A1 | 9/2008 | Hoke | |
| 2009/0056709 A1* | 3/2009 | Worsoff | 128/200.24 |
| 2009/0281454 A1 | 11/2009 | Baker et al. | |
| 2010/0049225 A1* | 2/2010 | To et al. | 606/159 |

OTHER PUBLICATIONS

Brown, Christopher L., and Scott M. Graham. "Nasal irrigations: good or bad'?." Current opinion in otolaryngology & head and neck surgery 12.1 (2004): 9-13.*

"Ayr Saline Nasal Mist." BF Ascher Company Inc RSS. Web. Jun. 3, 2016. <http://bfaschercom/products/ayr-saline-nasal-mist/>.*

* cited by examiner

DEVICE AND METHOD FOR CLEANING NASAL CAVITIES

FIELD OF THE INVENTION

The present invention relates generally to cleaning of body cavities and specifically to cleaning of the nasal cavities by creating fluid dynamic flow fields and generating mechanical stresses sufficient to achieve cleaning of the surface of the cavity of bacteria.

BACKGROUND OF THE INVENTION

A human body houses a variety of bacteria. *Staphylococcus aureus* is a group of bacteria usually found in the human armpit, groin, nose and throat. The nares (nostrils) are heavily colonized predominantly with *Staphylococcus epidermidis* and corynebacteria. About 20% of the population carries *Staphylococcus aureus* in the nose.

Around 1960, methicillin, an antibiotic closely related to penicillin, was introduced to treat *Staphylococcus* infections. Shortly thereafter, a strain of Staph developed that was resistant to methicillin. Methicillin-resistant *Staphylococcus aureus* (MRSA) is typically resistant to the synthetic penicillins (methicillin, oxacillin, nafcillin), cephalosporins and other antibiotics, such as erythromycin, clindamycin, aminoglycosides, and quinolone. MRSA is usually responsive to vancomycin. Recently, however, a few strains of *Staphylococcus aureus* have developed some degree of resistance to vancomycin. The vancomycin-resistant strains may be more difficult to treat.

MRSA infections have increased since 1990. Many patients with MRSA remain colonized indefinitely. MRSA lives in the nose of about 1%-2% of people (U.S. Centers for Disease Control and Prevention), usually without causing harm.

People colonized with MRSA can spread MRSA to other people. When a person has a break in the skin that is exposed to MRSA, an infection develops that is difficult to treat. Patients have a 30-60% risk of infection following colonization. MRSA colonization and infections have a significant impact on hospital and nursing homes. Because of its resistance to antibiotics, management of MRSA infections requires more immediate, complicated, toxic, and usually expensive treatment.

Cleaning the nasal membranes reduces MRSA colonization and decreases the chance of infection and the spread of MRSA. Current methods to clean the nasal membranes require improvement. The nose has two cavities, separated from one another by a wall of cartilage called the nasal septum. The external openings are known as nares or nostrils. Cleaning the nasal cavities is a difficult process because applying the necessary mechanical action to clean the nasal cavities requires enough pressure to clean, but care must be taken not to tear the membrane.

Current methods to clean nasal membranes include scraping, sponging, and the like. Devices are also available that use a solution or water to rinse the membranes. These devices provide incomplete cleaning. A device that combines mechanical action with rinsing would be an effective combination. A mechanical action/rinsing device that provides hydrodynamic flow within the nasal cavity where the fluid is suctioned and contained is needed to completely cleaning the nasal cavity membranes. A flow pattern that cleans in conjunction with mechanical action at a given area of the membrane would decrease the amount of bacterial colonization in the nose of a MRSA carrier.

It would be beneficial to find a better way to properly, repeatedly and consistently clean the nasal membranes of MRSA carriers. In order to clean the nasal membranes in a reasonable period of time, a device must provide sufficient surface area of the mechanical cleaner to accomplish its task. Both the mechanical action and the solution used to cleanse the membranes must be sterile and not provide further contamination of the membranes. A disposal tip capable of providing the mechanical action and delivering a sterile fluid is desirable. A device that introduces a jet of liquid to the membrane that applies the fluid intermittently with the aid of a motor is desirable. The jet action effects dislodging of bacteria due to the mechanical impact forces of the liquid, and the dislodged bacteria are then removed through suction and stored for disposal.

SUMMARY OF THE INVENTION

The invention is a device and method for cleaning nasal cavity membranes. The device deposits and collects a solution at a membrane of a nasal cavity. The device comprises a body having a coupling for releasably attaching a head. A neck or extension is included between the body and the head. The head is rotatable about a horizontal axis and fits within the nasal cavity. The head is shaped to accept replaceable covers that gently clean the nasal membranes. The device comprises fluid ejector outlets and suction inlets. The outlets are connected to a fluid container inside the body. The fluid container is filled with the solution. The fluid is moved from the container to the outlets via an aqueous pump. The inlets are connected to a suction chamber inside the body. The suction chamber is connected to a vacuum pump. The solution is pumped from the fluid container to the outlets and sprayed on the membranes at a delivery rate, which is variable via a control switch. The inlets suction the sprayed solution. The recovered solution is stored in the suction chamber.

The fluid ejector outlets generate streams of fluid that mechanically remove surface contaminants, including bacteria, from the nasal membrane. The contaminants are suctioned with the solution and stored in the suction chamber until discarded or captured by the replaceable covers, which are then discarded.

The method includes steps of:
inserting a fluid cartridge into the fluid container (alternatively, the fluid container can be filled manually),
inserting a disposable collection unit inside the suction chamber,
covering the head of the device with a disposable cover,
introducing the covered head into one nostril,
turning the power on so that the pump delivers fluid from the container through the neck to the head. A vacuum pump that creates suction at the inlets to the suction chamber is also activated. Outlets in the head spray solution onto the membranes from various points about the head. The neck rotates the head so that the cover gently brushes the nasal membranes. The neck rotates the head at a speed sufficient to generate mechanical stresses for the removal of contaminants from the nasal membranes. The spray washes the contaminants from the nose as the inlets suction the discharged spray and the contaminants. The discharge is stored in the disposable collection unit inside the suction chamber. After cleaning for about 0.5 to 3 minutes, the device is powered down.
the cover is discarded and a new cover fitted to the head, the cleaning is repeated for the other nostril. After both nostrils are cleaned, the device is powered down and the disposable collection unit containing the stored discharge fluid is removed and discarded.

The present invention describes novel devices and methods based on harnessing certain types of fluid dynamics to clean nasal membranes. The devices and methods of the present invention are effective, less costly, less time consuming, and potentially provide better cleaning than the art. The ability to nasal cavities effectively demonstrates one of the improvements of this invention over the art. This invention also improves over the art through a new approach of safely cleaning MRSA from the nasal passages by combining fluid dynamics that provide turbulent flow with a gentle mechanical brushing to clean the nasal cavity.

As used herein, "approximately" means within plus or minus 25% of the term it qualifies. The term "about" means between ½ and 2 times the term it qualifies.

The methods of the present invention can comprise, consist of, or consist essentially of the essential elements and limitations of the invention described herein, as well as any additional or optional ingredients, components, or limitations described herein or otherwise useful in compositions and methods of the general type as described herein.

All references to singular characteristics or limitations of the present invention shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

BRIEF DESCRIPTION OF THE DRAWINGS

FIG. 2 is a perspective view of an embodiment with the cap shown in see-through.

FIG. 3A is a blow-out view of the rotation means.

DETAILED DESCRIPTION OF THE INVENTION

Figure 1:
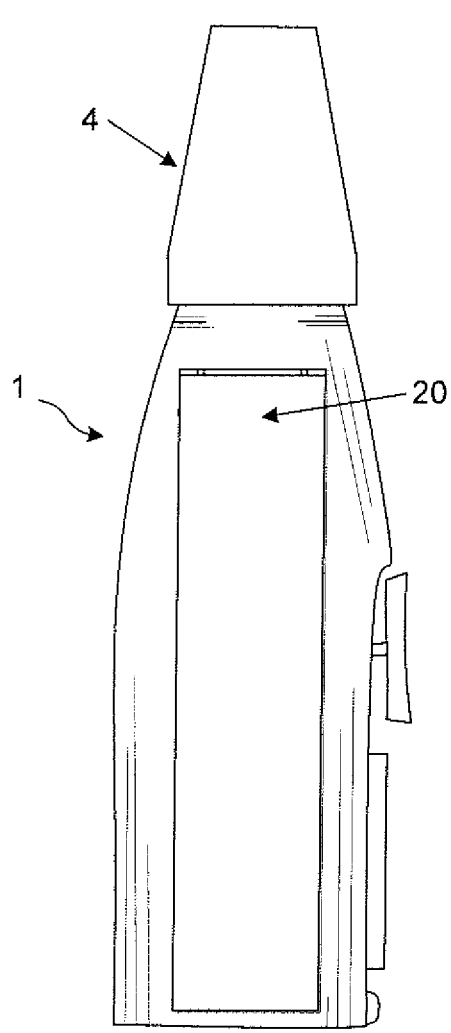
FIG. 1 is a perspective view of an embodiment with a cap in place.
Figure 2:
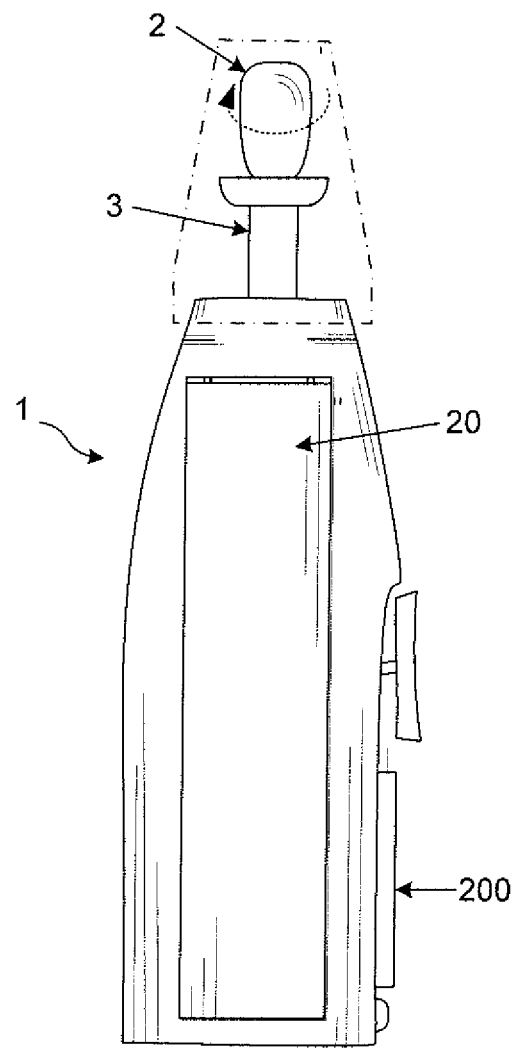

FIGS. 1 and 2 depict a nasal membrane cleaning device according to an embodiment of the invention. The cleaning device comprises a body 1, a head 2, and a neck 3 connecting the head to the body. A removable cap 4 covers the head and/on neck when not in use.

Figure 3:
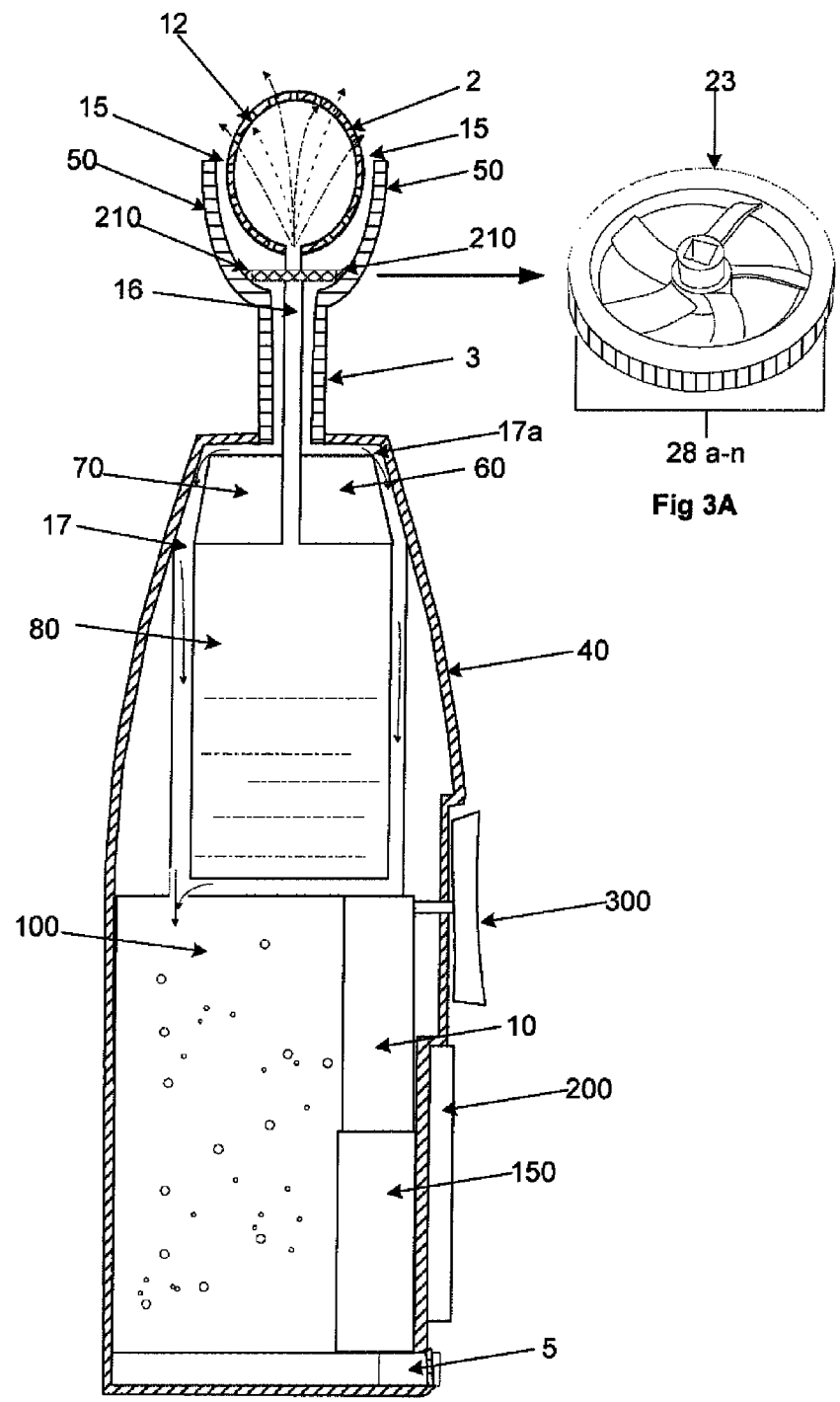
FIG. 3 is an overall schematic diagram of an embodiment of the present invention.

As depicted in FIG. 3, disposed in the housing of the body 1 is a processor 10 connected to a power source 5. The body 1 is water resistant shell 40 with a neck 3 for connecting the head. The neck typically extends from a first end of the body. The power source 5 (recharger, batteries or electric cord) is located at the opposite end of the body. The shell 40 is preferably made of a durable material, such as injection molded plastic, silicone, other polymers and/or metals.

The body 1 comprises means to access the interior of the shell 40, such as but not limited to a hinged door 20, screw compartment, snap in place component and the like.

Referring to FIG. 3, The fluid dispensing system includes a fluid reservoir 80 in communication with a pump 70 powered by a motor 150. in an embodiment, the fluid reservoir 80 has a capacity of about 10 ml to about 500 ml, preferably, about 100 to about 400 ml. The fluid reservoir 80 may include a moveable floor to aid in dispensing the fluid. The fluid reservoir 80 many include more than one compartment to mix separate solutions together to provide the desired fluid. When the pump 70 is activated, fluid is pumped from the fluid reservoir 80 through a conduit network 16 and delivered to outlets 12 in the head. The circuitry within the device (not shown) is programmed such that when a sensor (not shown) within the reservoir determines that the fluid is depleted, in addition to alerting the user via a control panel 200, the device is automatically shut off. When fluid is depleted from the fluid reservoir, the reservoir may be re-filled and/or replaced.

As the fluid is sprayed from the outlets, the discharged fluid is suctioned back into the device via inlets 15 positioned near the outlets. The suction inlets 15 are arranged around the neck below the head to collect the fluid sprayed on the nasal membranes. Discharged fluid is collected by suction inlets 15 via action of a wet vacuum pump 60 powered by a motor 150 and delivered to a suction chamber 100 for containment, handling and disposal. The inlets 15 may also include screens or apertures that prevent large materials from clogging the waste collection. In operation, waste travels through the inlets 15 by virtue of the force of the vacuum pump 60 through channels 17, 17a and is then deposited within the suction chamber 100. The inlets may comprise restrictions that increase the suction produced by operation of the wet vacuum pump 60 to enhance the suction of sprayed solution. while FIG. 3 depicts two channels 17, 17a, any configuration that pumps fluid from a first container and returns fluid to a second container is applicable.

Discharged solution, which is collected by suction inlets 15 via action of a wet vacuum pump 60, is delivered to a suction chamber 100 for containment, handling and disposal. All of the waste material collected by the device is stored within the suction chamber 100. An indicator located on a control panel 200 of the device alerts a user when the suction chamber 100 is full. The circuitry within the device (not shown) is programmed such that when a sensor (not shown) within the suction chamber 100 determines that the suction chamber 100 is full, in addition to alerting the user, the device is automatically shut off.

To discard the contents of a full suction chamber 100, a user presses a button (not shown) located on the shell control panel 200. The suction chamber 100 is removed/slides out from the device and can be emptied, cleaned and replaced. In another embodiment, the suction chamber 100 is disposable and discarded, and a new suction chamber 100 is then placed in the device.

Figure 4:
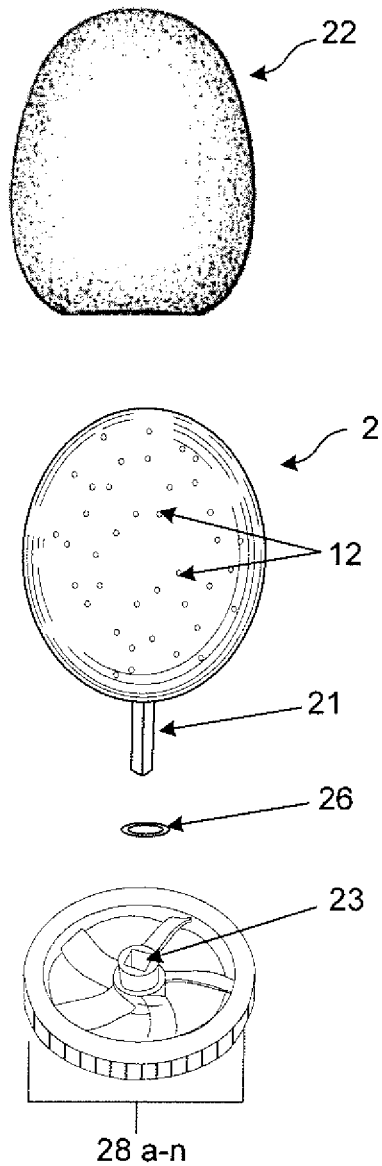
FIG. 4 is a perspective view of an embodiment of a head with a cover in relation to the rotation means.
Figure 5:
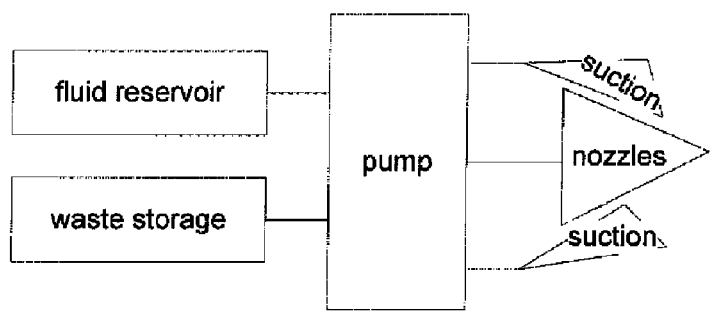
FIG. 5 is diagram of certain actions of the invention.
Figure 6:
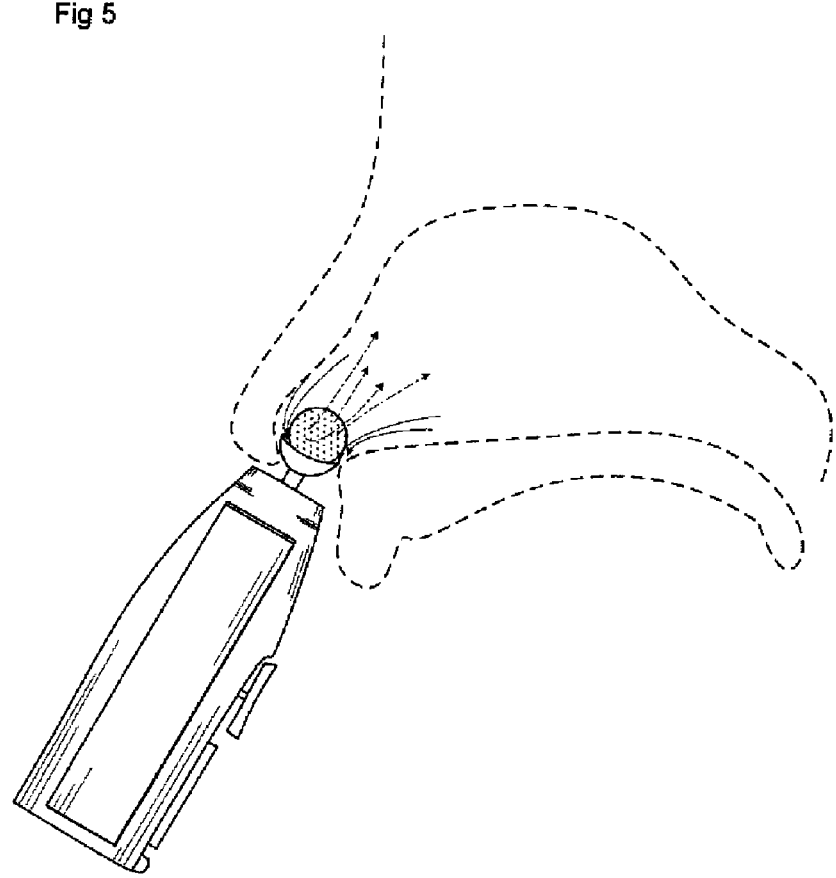
FIG. 6 is a depiction of the device in use.

Referring to FIG. 4, in an embodiment, the head 2 is disposable and formed of a soft, low-density open cell foam, such that the head 2 is easily deformable and provides outlets 12 for the solution. The head 2 has a textured outer surface, such as is characteristic for a soft open cell foam product. The head 2 may be constructed of a variety of materials that provide deformability and resiliency. The head has a lower hardness than the membrane to avoid abrasion. It is preferred that the head be formed from a foam-like material, such as polyurethane foam, particulate-filled polymers, as well as various natural and synthetic sponge materials. It is preferred that the foam-like material has a low density. The head may be a hollow sphere with opening for outlets 12. The head preferably has a generally smooth surface with no protrusions or embedded particulates/fillers that could scratch the membrane. The head is resistant to chemicals.

The head is preferably long enough to access the area to be cleaned, yet short enough to fit within the nasal cavity. The head cross-sectional profile creates convergent and divergent flows as it moves over the membranes such that effective shear stress is generated to clean the membranes. The head profile is preferably circular or elliptical shaped. Circular geometry may also be useful to facilitate the conditions of convergent and divergent flow field as the head moves/rotates within the nasal cavity.

In an embodiment, the head is designed for ease of insertion into the nasal opening. In an embodiment, the angle between the head and the nasal membrane is about 180 degrees. The gap between the head and the nasal membrane is preferably small to position of head so that the rotating head touches a side of the nasal cavity when moved slightly by the operator. Flexibility of the head is low so that the head is approximately parallel to the surface to be cleaned such that a small and uniform narrow gap/distance is maintained during the motion of the head. Distortion or wobbling of the head is achieved by materials selection and by the thickness of the head. In an embodiment, the distal end of the head is thinner than the remainder of the head to increase its flexibility.

Head shape increases turbulence to sweep contaminants from the nasal membranes and create flow fields onto the membrane and back into the inlets. In an embodiment the head is shaped to provide a uniform and minimal gap within the nares in a vertical direction. The distal end of the head is rounded to facilitate insertion and prevent membrane scratching.

In an embodiment, the head 2 is a multiuse head. In an embodiment depicted in FIG. 4, the head is formed from a rubberized plastic and includes a disposable cover 22. The disposable cover slips over the head 2 and is secured using connectors, such as hook and loop material, snaps, or an elastic material forming a band elastic. In an embodiment, the cover 22 is an elasticized generally U-shaped material that firmly grips the head without the use of adhesive. The cover 22 may be formed of a pair of sheets, forming a front and a back having an interconnection. In an embodiment, the cover 22 is formed of a spun-lace non-woven sheet. The cover may be single-layer, multiple-layer, with or without reinforcement scrim, textured, and/or untreated or pretreated with a variety of materials. The cover outer surface may be tufted, flocked, or frayed to provide additional cleaning abilities. As will be clear to those of skill in the art, the outer surfaces of the covers may be configured in a variety of ways, and may have a variety of textures or treatments.

The head and/or the cover may be coated, incorporate a controlled release substance or otherwise surface treated. Some non-exclusive coatings examples include biocides, wetting agents, lubricants, and the like.

In an embodiment, the head is a generally spherical or oblong shape and comprises outlets 12 to spray solution from the head. The head may also take various other forms, provided the head fits within the nares and contacts or nearly contacts the nasal membranes. In an embodiment the outlets are openings formed in the foam in the head. In an embodiment, the outlets are nozzles. Having the cover and/or head disposable is provided so that the cover or head is used once and disposed of when soiled. A new cover/head is then placed on the head/body. The head cover has a tensile strength, tear strength, and hardness tear strength sufficient to avoid breaking apart during use.

In an embodiment, the head 2 is releasably connected to the neck 3 via a connector 21. The connector is a hollow, hard plastic piece that extends from the head. In an embodiment, the connector has flat external sides. In an embodiment, the connector forms a fluid conduit to the outlets 12. In an embodiment where the head is a hollow sphere, the connector provides solution to the sphere, where it is then forced through the outlets 12 by the force of the pump 70. The connector and or the neck may be straight or on an angle. The neck should have some flexibility to avoid trauma to the nasal membrane; however, the connector has to be rigid enough to avoid excessive vibrations and to maintain contact with the membrane.

As shown in FIG. 3A and FIG. 4, the connector 21 inserts into a rotor 23 located in the neck 3. The connector 21 can be attached to, and detached from, the rotor 23 by insertion. Preferably, the connector 21 is a quick connect coupling that connects to the rotor 23. For example, there can be a quick connect on the connector, the rotor, or both. Examples of couplings include threads, a chuck, a friction sleeve, a non-circular profile to resist rotation, and the like. The rotor is a gear that is turned by a gear mechanism 210 powered by a motor 150 in the body of the device. In an embodiment, the connector 21 also maintains the position of the head relative to the surface to be cleaned. The rotor has a circular ring of gear teeth 28 a-n that engage with the gear mechanism 210. An O-ring 26 is positioned above the rotor so that when the head 2 is attached to the neck 3, it forms a seal.

The pressure asserted on the fluid as it exits the outlets is about 0.5 psi to about 30 psi, preferably about 3-10 psi. Fluid flow rate is about 10 ml/s to about 60 ml/s, preferably about 20 ml/s to about 40 ml/s. If a greater number of outlets are provided, a greater flow rate would be required to maintain the optimum velocity. Pulse frequency is about 0.5 Hz to about 50 Hz, preferably from about 5 Hz to about 25 Hz. Delivery pulse duty cycle may be from about 10% to 100%, preferably from about 40% to about 60%. Where the cycle is 100% a continuous flow of fluid is produced. Delivery pulse volume is about 0.1 ml to about 5 ml, preferably from about 0.5 ml to about 2 ml.

The rotational speed of the head is about 1,000 rpm to 15,000 rpm, preferably from about 5000-9000 rpm. The device has the ability to rotate the head in either direction around a vertical axis. The speed of the motor is matched to the velocity of gear, which is transferred to the head. The rotational speed is low enough so as to avoid damage to the head or the membranes, but high enough to gently abrade the nasal membrane.

In operation, the user removed the removable cap 4 and switches the device on using the control button 300 located on the body 1 of the device. The control panel 200 is connected to the circuitry within the device for making various electrical operations, such as direction of rotation, speed of rotation, spray velocity, pulsation rate, warming of the solution and the like, available to the user. Switching the device on activates the motor 150 causing the pumps to activate and activating the gear to turn the head. The pump 70 forces the fluid from the fluid reservoir 80 to the head and through the outlets 12. In an embodiment, the outlets spray enough fluid on to the nasal membrane to ensure flow around the head, and preferably in sufficient volume to also dislodged contaminants.

The rotation of the head gently rubs the nasal membrane to remove debris. The fluid with debris is returned to the device through the suction inlets 15 by the action of the wet vacuum pump 60 and stored in the suction chamber 100. Vacuum duty cycle is about 10% to 100%, preferably from about 50% to 100%. Fluid delivery to vacuum ratio is about 1:1 with a small amount of spray not recovered by the inlets.

During operation, the user places the head slightly inside the nostril. When cleaning the membranes, a user actuates a control button 300 to produce a solution spray through outlets 12 in order to cover the membrane with solution. Cover 22 or the head 2 gently brushes the surface to dislodge debris. The head 2 is configured and moving in a direction whereby the spray passes over the membrane first, the cover 22/head 2 loosens debris, and the spray is collected by the inlets 15. Debris is removed. The trajectory angle of the spray varies as the head rotates to position the sprayed solution near the inlets. In an embodiment, the head rotates in the nasal cavity a small distance from the membrane. In an embodiment, the exterior of the inlets help position the head in the cavity. The exterior structure of the inlets positions the device within the nares at the nostril opening to steady the head against sudden movement.

To diminish sprayed fluid from leaking from the nares, the neck comprises a splash guard 50. The splash guard fills the opening of the nares and deflects fluid and contaminants from the nasal membrane into the inlets. the splash guard is relatively flexible for comfort to the user.

The user then inserts the head into the second nostril and repeats the cleaning. The disposable head cover may be replaced in between cleaning each nostril. After completion, the device is shut off, the suction chamber 100 removed, cleaned and replaced, and the fluid reservoir 80 refilled or replaced. The wet vacuum pump 60 operates to collect most of the contaminated fluid from the nares. The contaminated fluid collected in the suction chamber 100 is contained to prevent exposure of the contaminated fluid to the environment.

In an embodiment, the fluid is a sterile saline. In an embodiment, the fluid is a sterile buffered hypertonic saline solution. In an embodiment, the fluid comprises purified water, sodium chloride, disodium hydrogen phosphate, and potassium dihydrogen phosphate. The pH of the fluid is from about 5 to about 7, preferably, about 5.5 to about 6.5.

The foregoing description of the invention has been presented for purposes of illustration and description. It is neither intended to be exhaustive nor to limit the invention to the precise form disclosed. Many alternatives, modifications, and variations will be apparent to those skilled in the art. For example, the terms: cleaning and rotation are not meant to limit the overall invention. Such terms can include modifications or combination with other methods, such as air, vibrations, heat and the like. While surface cleaning is a major application of this invention, other surface modifications such as coating (with a drug or medication) and disinfection are possible. Accordingly, this invention is intended to embrace all alternatives, modifications, and variations that fall within the spirit and broad scope of the claims.

I claim:

1. A nasal membrane cleaning device for cleaning a nasal membrane comprising:
   a body, a rotating head and a neck connecting the head to the body;
   the head including a plurality of outlets through which fluid is sprayed during use of the device, the head having a smooth surface without protrusions or embedded particulates or fillers that could scratch the nasal membrane during use;
   the body housing a motor, a pump, a vacuum pump, a fluid reservoir and a suction chamber, wherein the motor is adapted for powering the pump, and the pump is in communication with said fluid reservoir such that, when the pump is activated, the fluid contained in the reservoir is forced through a conduit network to said outlets for delivery onto the nasal membrane of a user; and
   the neck including a splash guard and fluid inlets located below the head and in communication with the vacuum pump and the suction chamber, wherein the splash guard is configured to deflect the fluid into the inlets;
   the head further comprising a hollow connector that comprises part of the conduit network through which the fluid is delivered from the reservoir to the outlets;
   the cleaning device configured such that the head is insertable into a user's nasal opening, with the head adapted for powered rotation about a vertical axis to rub a user's nasal membrane to remove debris located at the nasal membrane, without damaging the nasal membrane, while the fluid from the fluid reservoir is sprayed from said outlets onto the user's nasal membrane and thereafter the fluid along with the debris removed from the user's nasal membrane is suctioned through said inlets into the device and into the suction chamber.

2. A method of using the device of claim 1 having the fluid in said reservoir to clean the nasal cavity of a user, comprising the steps of:
   introducing the head of the device into one nostril such that said splash guard fills the opening of the nostril;
   powering on the device so that the pump delivers the fluid from the reservoir through the neck to the head and through the outlets, while the head rotates so that it rubs against the nasal membrane, thereby cleaning the nasal membrane of the debris without damaging the nasal membrane; and
   suctioning the fluid sprayed out of the outlets and the debris removed from the nasal membrane into the suction chamber where it is stored.

3. The method of claim 2 wherein the fluid in the reservoir comprises a sterile saline solution.

4. The method of claim 2 wherein the fluid in the reservoir comprises purified water, sodium chloride, disodium hydrogen phosphate, and potassium dihydrogen phosphate.

5. The method of claim 2 wherein the fluid in the reservoir has a pH from about 5 to about 7.

6. The method of claim 2, further comprising the steps of:
   prior to cleaning the nasal cavity, inserting a disposable collection unit inside the device and covering the head of the device with a disposable cover; and
   after cleaning the nasal cavity, removing the collection unit containing the fluid and the debris cleaned from the nasal membrane.

7. The cleaning device of claim 1 wherein the head comprises a shape that provides a uniform gap and a minimal gap between the nasal membrane and an exterior of the head.

8. The cleaning device of claim 1 wherein the head further comprises a disposable cover.

9. The cleaning device of claim 8 wherein the disposable cover comprises a coating selected from the group consisting of a biocide, a wetting agent, and a lubricant.

10. The cleaning device of claim 1 wherein the outlets spray the fluid from the reservoir onto the nasal membrane from multiple points about the head.

11. The cleaning device of claim 1 wherein the head is rotatable at a speed sufficient to generate a mechanical stress to remove the debris from the nasal membrane.

12. The cleaning device of claim 1, further comprising a rotor, wherein said connector engages with the rotor for causing the head to rotate.

13. A nasal membrane cleaning device, comprising:
a body housing a pump, a fluid reservoir for containing fluid to be discharged from the device onto a user's nasal membrane, and a suction chamber for receiving used fluid and debris collected after discharge from the device;
a head adapted for insertion into a user's nostril and powered rotation therein, said head mounted above said body and including a plurality of outlets in fluid communication with said fluid reservoir, wherein the head is formed of a deformable and resilient material that provides said plurality of outlets;
a power source for powering the rotation of said head and the pumping of the fluid from said fluid reservoir to said outlets such that the fluid from said fluid reservoir can be sprayed from said outlets onto a user's nasal membrane while the head rotates; and
fluid inlets arranged below and external to said head, said inlets in fluid communication with said suction chamber;
wherein the cleaning device is configured such that the head is insertable into a user's nasal opening, and thereafter the head caused to rotate about a vertical axis to rub a user's nasal membrane to remove the debris located on the nasal membrane, without damaging the nasal membrane, while the fluid from the fluid reservoir is sprayed from said outlets onto the user's nasal membrane and thereafter the fluid along with the debris removed from the user's nasal membrane is suctioned into the device through said inlets and into the suction chamber.

14. The nasal cleaning device of claim 13, further comprising a splash guard configured to deflect the discharged fluid into the inlets, said splash guard arranged in spaced-apart relationship with said head such that the discharged fluid is directed to the inlets between the splash guard and the head.

15. A method of using the device of claim 13 having the fluid in said reservoir to clean the nasal cavity of a user, comprising the steps of:
introducing the head of the device into one nostril;
activating the device so that the pump delivers the fluid from the reservoir to the head and through the outlets, while the head rotates so that it rubs against the nasal membrane so as to clean the debris from the nasal membrane without damaging the nasal membrane, and the fluid sprayed out of the outlets and the debris removed from the nasal membrane is suctioned into the suction chamber.

16. The nasal membrane cleaning device of claim 13, wherein said head is formed of a low-density, open-cell foam.

17. The nasal membrane cleaning device of claim 13, wherein the head further comprises a disposable cover.

18. A nasal membrane cleaning device, comprising:
a body housing a fluid reservoir for containing fluid to be discharged from the device onto a user's nasal membrane, and a suction chamber for receiving used fluid and debris collected after discharge from the device;
a head adapted for insertion into a user's nostril and powered rotation therein, said head mounted above said body and including a plurality of outlets in fluid communication with said fluid reservoir, the head having a smooth surface without protrusions or embedded particulates or fillers that could scratch the nasal membrane during use;
a power source for powering the rotation of said head and the pumping of the fluid from said fluid reservoir to said outlets such that the fluid from said fluid reservoir can be sprayed from said outlets onto a user's nasal membrane while the head rotates;
fluid inlets arranged adjacent and external to said head, said inlets in fluid communication with said suction chamber; and
a splash guard configured to deflect the discharged fluid into the inlets, said splash guard arranged in spaced-apart relationship with said head such that the discharged fluid is directed to the inlets between the splash guard and the head;
wherein the cleaning device is configured such that the head is insertable into a user's nasal opening, and thereafter the head caused to rotate about a vertical axis to rub a user's nasal membrane to remove debris located on the nasal membrane, without damaging the nasal membrane, while the fluid from the fluid reservoir is sprayed from said outlets onto the user's nasal membrane and thereafter the fluid sprayed from said outlets along with the debris removed from the user's nasal membrane is suctioned through said inlets into the device and into the suction chamber.

19. A method of using the device of claim 18 having the fluid in said reservoir to clean the nasal cavity of a user, comprising the steps of:
introducing the head of the device into one nostril;
activating the device so that the pump delivers the fluid from the reservoir to the head and through the outlets, while the head rotates so that it rubs against the nasal membrane so as to clean the debris from the nasal membrane without damaging the nasal membrane, and the fluid sprayed out of the outlets and the debris removed from the nasal membrane is suctioned into the suction chamber.

20. The nasal membrane cleaning device of claim 18, wherein the head further comprises a disposable cover.

* * * * *